(12) United States Patent
Janac et al.

(10) Patent No.: US 8,577,627 B1
(45) Date of Patent: Nov. 5, 2013

(54) CABLE TENSIONING CYCLING SYSTEM

(75) Inventors: Joe R. Janac, Bryan, TX (US); James H. Stasny, Bryan, TX (US)

(73) Assignee: Dynacon, Inc., Bryan, TX (US)

( * ) Notice: Subject to any disclaimer, the term of this patent is extended or adjusted under 35 U.S.C. 154(b) by 564 days.

(21) Appl. No.: 12/886,762

(22) Filed: Sep. 21, 2010

Related U.S. Application Data (60) Provisional application No. 61/244,563, filed on Sep. 22, 2009.

(51) Int. Cl.
*G01L 5/04* (2006.01)
*G01P 3/02* (2006.01)
*G21C 17/00* (2006.01)

(52) U.S. Cl.
USPC ............ 702/43; 702/142; 702/183; 702/189; 242/419.9

(58) Field of Classification Search
USPC .................. 702/43, 142, 183, 189; 242/419.9
See application file for complete search history.

(56) References Cited

U.S. PATENT DOCUMENTS

| | | | | |
|---|---|---|---|---|
| 3,618,897 A | * | 11/1971 | Swoboda et al. | 254/270 |
| 4,504,023 A | * | 3/1985 | Lauritzen | 242/412 |
| 7,913,944 B1 | * | 3/2011 | Lombardi et al. | 242/419.7 |

* cited by examiner

*Primary Examiner* — Alexander H Taningco
*Assistant Examiner* — L. Anderson
(74) *Attorney, Agent, or Firm* — Patterson & Sheridan, L.L.P.

(57) ABSTRACT

A hydraulic operated system for testing cable under variable tensions and speeds with a lower input horsepower requirement. The system can include storage reels in series with multiple moveable sheaves. A moveable tensioning moveable sheave can be in series with the multiple moveable sheaves for receiving cable and for measuring load and speed of the cable using sensors. The system can include clutches and a clutch controller. The measured load and speed can be transmitted to a processor which can perform calculations and comparisons thereon, and can transmit related notifications to client devices through a network.

9 Claims, 4 Drawing Sheets

FIG. 6 a# CABLE TENSIONING CYCLING SYSTEM

CROSS REFERENCE TO RELATED APPLICATIONS

The present application claims priority and the benefit of co-pending U.S. Provisional Patent Application Ser. No. 61/244,563 filed on Sep. 22, 2009, entitled "CABLE TENSIONING CYCLING SYSTEM", which is incorporated herein in its entirety.

FIELD

The present embodiments generally relate to a hydraulically and/or electrically operated system for testing cable under variable tensions and speeds with lower input horsepower requirements.

BACKGROUND

A need exists for a system that can cycle test long-length cable samples at variable cable tensions and speeds.

A need exists for a system that can reduce the amount of horsepower required to cycle cable.

A need exists for a closed loop tensioning system that can effectively close the loop and allow cable to be tensioned and cycled with less horsepower.

The present embodiments meet these needs.

BRIEF DESCRIPTION OF THE DRAWINGS

The detailed description will be better understood in conjunction with the accompanying drawings as follows.

The present embodiments are detailed below with reference to the listed Figures.

DETAILED DESCRIPTION OF THE EMBODIMENTS

Before explaining the present system in detail, it is to be understood that the system is not limited to the particular embodiments, and the system can be practiced or carried out in various ways.

The present embodiments relate to a hydraulically and/or electrically operated system for testing cable under variable tensions and speeds with a lower input horsepower requirement.

The present embodiments further relate to a hydraulic operated system that can include: a first storage reel, a second storage reel, a first moveable sheave, a second moveable sheave, a third moveable sheave, a fourth moveable sheave, a first clutch, a second clutch, a clutch controller, and a moveable tensioning moveable sheave.

One or more embodiments relate to a long-length cable sample testing system. The system can utilize a parallel moveable sheave system and a hydraulically and/or electrically powered tensioning turning sheave assembly that allows for transfer of long-cable sample lengths at variable cable tensions and speeds with a low input horsepower. The system can be used for from about a few hundred feet of cable to about several miles of cable in a single setting. The system can require a lower amount of horsepower to move cable for testing as compared to normal systems known in the art.

A first storage reel can be used for paying out cable to be tested. The first storage reel can be adapted to apply tension to the cable, and to allow the tension in the cable to be multiplied up to a test tension.

The system can include a first moveable sheave in series with a second moveable sheave. The first moveable sheave can be rotated by a first hydraulic drive or a first electric drive. The second moveable sheave can be rotated by a second hydraulic drive or a second electric drive. The first moveable sheave can receive the cable and can pass the cable to the second moveable sheave.

The third moveable sheave can be in series with a fourth moveable sheave. The third moveable sheave can be rotated by the second hydraulic drive or the second electric drive. In embodiments, the third moveable sheave can be in parallel with the second moveable sheave. The fourth moveable sheave can be rotated by the first hydraulic drive or the first electric drive, and can further be in parallel with the first moveable sheave.

In embodiments, each moveable sheave can have grooves for receiving the cable and for containing the cable in each of the grooves. In one or more embodiments, each sheave can have at least six grooves. The grooves can be disposed in parallel, and can transfer the cable from one moveable sheave to another moveable sheave without otherwise touching or contacting additional cable.

Both the second moveable sheave and the third moveable sheave can be tilted in part, thereby enabling at least two opposing grooves to be lined-up or aligned at bottoms of the sheaves, but to be offset at tops of the sheaves to facilitate cable transfer without sliding the cable on a face of the moveable sheaves.

The second moveable sheave and the third moveable sheave can be connected and/or coupled with a first clutch. The first clutch can be operated by the second hydraulic drive. The first clutch can also disengage the second moveable sheave from the third moveable sheave.

The first moveable sheave and a fourth moveable sheave can be connected and/or coupled with a second clutch. The second clutch can be operated by the first hydraulic drive. The second clutch can disengage the first moveable sheave from the second moveable sheave. The first clutch and the second clutch can be controlled by a clutch controller that can be in communication with a power source. Each clutch can be operable by one of the drives, a hydraulic power source, or combinations thereof.

A first friction material can be disposed between the first moveable sheave and the fourth moveable sheave. A second friction material can be disposed between the second moveable sheave and the third moveable sheave. The friction material can provide coupling of each pair of moveable sheaves with the clutch. The first friction material and the second friction material can include a wearable brake material that can lock each pair of moveable sheaves together during testing of the cable.

The hydraulic drives and/or electric drives can be connected to or coupled with a moveable tensioning moveable sheave, also referred to as a moveable tensioning sheave. In embodiments, the moveable tensioning sheave can include a load measuring sensor and a speed detector.

In embodiments, each of the hydraulic drives can have at least one hydraulic pump connected to a hydraulic motor for rotating each moveable sheave. From about one hydraulic pump to about eight hydraulic pumps can be used in connection with each hydraulic drive. The hydraulic pump can have a fluid reservoir, and can be operated by an electric motor. The electric motor can be powered by an electric power source, such as a four hundred sixty volt three-phase power supply.

The moveable tensioning sheave can receive the cable from the second moveable sheave and can pass the cable to the third moveable sheave, which can sequentially pass the cable to the fourth moveable sheave.

In embodiments, a second storage reel can be used for receiving the cable and can be adapted to apply a second tension to the cable to be tested, which can allow the tension in the cable to be multiplied up to the test tension.

In embodiments, the cable can be wrapped or reeved around the first moveable sheave and the second moveable sheave five times prior to passing the cable to the moveable tensioning sheave. The cable can move from the moveable tensioning sheave to the fourth moveable sheave, and can then be wrapped or reeved around the third moveable sheave and the fourth moveable sheave five times prior to passing the cable to the second storage device.

The tensioning of the cable can occur at a speed from about one tenth of a foot per minute to about one thousand feet per minute. The tensioning of the cable can occur at a load from about one hundred pounds of force to about sixty thousand pounds of force.

In embodiments, a first electric drive and a second electric drive can be used to rotate the moveable sheaves in addition to, or in replacement of, the first and second hydraulic drives.

In embodiments, a hydraulic power source can be connected to the moveable tensioning sheave. The hydraulic power source can have at least one hydraulic pump connected to a hydraulic motor and/or a linear actuator. The hydraulic pump can have a fluid reservoir and can be operated by an electric motor, which can be powered by an electric power source.

The system can have a processor for receiving signals from the load measuring sensor and the speed detector. The processor can be in communication with a network, at least one client device, and a data storage. The network can include the internet, an intranet, a local area network, a wide area network, a virtual private network, a satellite network, a cellular network, other similar networks, or combinations thereof. The client devices can be laptops, cell phones, pagers, or another network. In embodiments, the client device can have computer instructions for continuous remote monitoring of one or more compared signals from one or more processors simultaneously. The client devices can be in communication with the processor through the network for receiving load signals, speed signals, compared signals, notifications, or combinations thereof.

Computer instructions can be located in the data storage and can be used for storing preset stress data for the cable to be tested. For example, data associated with loads that a cable can withstand can be stored in the data storage. Data associated with speeds that a cable can withstand can be stored in the data storage.

Computer instructions can be stored in the data storage to instruct the processor to compare received signals from the load measuring sensor and the speed detector to the stored preset stress data, thereby forming compared signals. The processor and can determine if the received signals exceed or fall below the stored preset stress data. For example, if the stored preset stress data includes a maximum load amount of one thousand pounds, and the measured and received load signal is a load of two thousand pounds, then the processor can determine that the preset stress data has been exceeded.

The system can have computer instructions in the data storage to instruct the processor to provide a notification when the compared signals exceed or fall below the stored preset stress data. For example, if the compared signals exceed or fall below the stored preset stress data, the processor can transmit the notification over the network to one or more client devices, thereby notifying users of the deviation from the stored preset stress data.

The system can include computer instructions to instruct the processor to display the compared signals, the notification, or combinations thereof within client devices.

In one or more embodiments, each drive of the system can be either a hydraulic drive or an electric drive. The first moveable sheave can be configured to receive the cable from the first storage reel. The first drive can be coupled with the first moveable sheave, and can be configured to rotate the first moveable sheave. The rotating first moveable sheave can be configured to pass the cable to the second moveable sheave in series with the first moveable sheave. The second moveable sheave can be configured to receive the cable from the first moveable sheave. The second drive can be coupled with the second moveable sheave, and can be configured to rotate the second moveable sheave. The moveable tensioning sheave can be coupled to at least one of the drives and can be disposed in series with the second moveable sheave. The second moveable sheave can be configured to pass the cable to the moveable tensioning sheave, which can be configured to receive the cable from the second moveable sheave. The third moveable sheave can be disposed in series with the moveable tensioning sheave, and can be configured to receive the cable from the moveable tensioning sheave. The second drive can be coupled with the third moveable sheave for rotating the third moveable sheave. The fourth moveable sheave can be disposed in series with the third moveable sheave and coupled with the first drive for rotating the fourth moveable sheave. The rotating fourth moveable sheave can be configured to receive the cable from the rotating third moveable sheave. The second storage reel can be configured to receive the cable from the fourth moveable sheave, and can be adapted to apply a second tension to the cable, thereby allowing tension in the cable to be multiplied up to the test tension.

Figure 1:
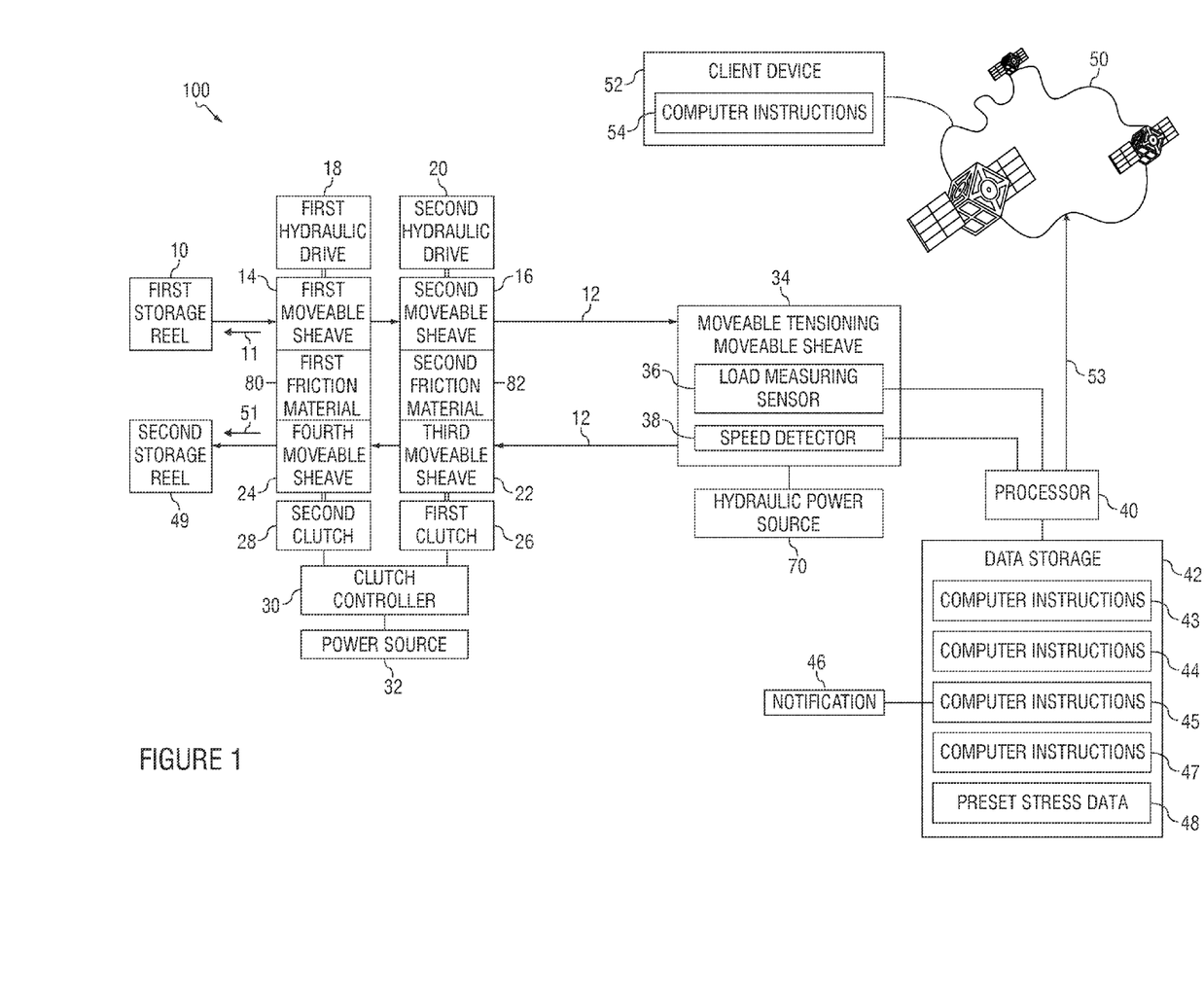
FIG. 1 depicts a schematic representation of an illustrative hydraulic cycle test system.

FIG. 1 depicts a schematic representation of an illustrative hydraulic cycle test system 100 according to one or more embodiments. The hydraulic cycle test system 100, which can also be referred to as a hydraulic operated system for testing cable under tension, can include one or more first storage reels 10, one or more first moveable sheaves 14, one or more first friction materials 80, one or more fourth moveable sheaves 24, one or more second clutches 28, one or more second moveable sheaves 16, one or more second friction materials 82, one or more third moveable sheaves 22, one or more first clutches 26, one or more first hydraulic drives 18, one or more second hydraulic drives 20, one or more clutch controllers 30, one or more power sources 32, one or more second storage reels 49, one or more moveable tensioning moveable sheaves 34, one or more hydraulic power sources 70, one or more client devices 52, and one or more processors 40 in communication with one or more data storages 42.

Each of the moveable sheaves 14, 16, 22, and 24 can have six grooves for receiving the cable 12 to be tested. The cable 12 can be contained in each of the grooves in parallel, thereby allowing for the transfer of at least a portion of the cable 12 from one moveable sheave to another moveable sheave without contacting additional portions of the cable 12. For example, grooves of the first moveable sheave 14 can contain the cable 12 as the cable 12 is transferred from the first moveable sheave 14 to the second moveable sheave 16. The grooves of the moveable sheaves can be tilted in part, thereby enabling at least two opposing grooves to be aligned at the bottoms thereof but offset at the tops thereof. The tilt of the grooves can facilitate the transfer of a portion of the cable 12 from one moveable sheave to another moveable sheave, and can prevent the portion of the cable 12 from sliding about the face of the associated moveable sheaves.

The first friction material 80 can be disposed between the first moveable sheave 14 and the fourth moveable sheave 24. The second friction material 82 can be disposed between the second moveable sheave 16 and the third moveable sheave 22. The first friction material 80 can couple together the first moveable sheave 14 and the fourth moveable sheave 24 with at least one of the clutches 26 and 28 utilizing a frictional force. The second friction material 82 can couple together the second moveable sheave 16 and the third moveable sheave 22 with at least one of the clutches 26 and 28 utilizing a frictional force. The friction materials 80 and 82 can include wearable brake material that can lock the pairs of moveable sheaves together during testing of the cable 12.

The first clutch 26 can connect the second moveable sheave 16 to the third moveable sheave 22. Accordingly, the first clutch 26 can disengage the second moveable sheave 16 from the third moveable sheave 22. In one or more embodiments, the first clutch 26 can be operated by the second hydraulic drive 20.

The second clutch 28 can connect the first moveable sheave 14 to the fourth moveable sheave 24. Accordingly, the second clutch 28 can disengage the first moveable sheave 14 from the fourth moveable sheave 24. In one or more embodiments, the second clutch 28 can be operated by the first hydraulic drive 18.

In one or more embodiments, the clutch controller 30 can control the first clutch 26 and the second clutch 28. The clutch controller 30 can be in communication with the power source 32.

The moveable tensioning moveable sheave 34 can be connected to and/or in communication with at least one of the hydraulic drives 18 and 20, the hydraulic power source 70, or combinations thereof. The moveable tensioning moveable sheave 34 can include a load measuring sensor 36 and a speed detector 38. The load measuring sensor 36 can be a stress gauge, a strain gauge, or a similar device for measuring load. The speed detector 38 can be tachometer, encoder, or similar device.

In operation, the first moveable sheave 14 can receive the cable 12 from the first storage reel 10. The second moveable sheave 16 can receive the cable 12 from the first moveable sheave 14. The moveable tensioning moveable sheave 34 can receive the cable 12 from the second moveable sheave 16.

In one or more embodiments, the processor 40 can be in communication with: the client device 52, the load measuring sensor 36, the speed detector 38, the data storage 42, or combinations thereof. Accordingly, the processor 40 can communicate with the client device 52, the load measuring sensor 36, and the speed detector 38. The processor 40 can receive signals from the load measuring sensor 36 and the speed detector 38 and can store the signals in the data storage 42. The processor 40 can monitor the tension loads of the cable 12, the speed of the cable 12, or combinations thereof.

The data storage 42 can have: computer instructions 43 to instruct the processor to store preset stress data for the cable 12; computer instructions 44 to instruct the processor to compare received signals from the load measuring sensor 36 and the speed detector 38 to the stored preset stress data, and to form compared signals; computer instructions 45 to instruct the processor to provide a notification 46 when the compared signals exceed or fall below the stored preset stress data; and computer instructions 47 to instruct the processor to display the compared received signals, the notification, or combinations thereof within the client device 52. The data storage 42 is shown with preset stress data 48 stored therein.

The processor 40 can be in communication with the client device 52 via a network 50. The network 50 can be the Internet, a local communication network, a satellite network, a cellular network, a wired network, a wireless network, or any other communication network. Data 53 is shown being transmitted from the processor 40 to the client device 52 over the network 50. The data 53 can include a notification, a load signal, a speed signal, a compared signal, other data associated with the cable, or combinations thereof.

The client device 52 can have computer instructions 54 to allow for continuous remote monitoring of a plurality of compared signals from the processor and/or a plurality of processors. The processor 40 can be in communication with a plurality of client devices simultaneously. The client device 52 can be a laptop, a cell phone, a pager, or another electronic device.

In operation, the cable 12 can be connected to the first storage reel 10 and to the first moveable sheave 14. Accordingly, the first storage reel 10 can be used to pay out the cable 12, and to apply a first tension 11 to the cable 12. Accordingly, the cable 12 can be tensioned up to a test tension.

The first hydraulic drive 18 can rotate the first moveable sheave 14 and the fourth moveable sheave 24. The second hydraulic drive 20 can rotate the second moveable sheave 16 and the third moveable sheave 22. Accordingly, the cable 12 can be passed from the first moveable sheave 14 to the second moveable sheave 16. For example, the cable 12 can be configured to reeve around the first moveable sheave 14 and the second moveable sheave 16, such as five times, after which the cable 12 can pass from the second moveable sheave 16 to the moveable tensioning moveable sheave 34. Within the moveable tensioning moveable sheave 34, the load measuring sensor 36 can measure the load on the cable 12, and the speed detector 38 can measure the speed of the cable 12, forming signals and transmitting the signals to the processor 40 for storage in the data storage 42. The moveable tensioning moveable sheave 34 can pass the cable 12 to the third moveable sheave 22.

The third moveable sheave 22 can be connected in series with the fourth moveable sheave 24, and in parallel with the second moveable sheave 16. The third moveable sheave 22 can be configured to be rotated by the second hydraulic drive 20. The fourth moveable sheave 24 can be in parallel with the first moveable sheave 14, and can be configured to be rotated by the first hydraulic drive 18. Accordingly, the cable 12 can pass from the third moveable sheave 22 to the fourth moveable sheave 24 as the moveable sheaves rotate. The cable 12 can then pass from the fourth moveable sheave 24 to the second storage reel 49. In one or more embodiments, the cable 12 can be configured to reeve around the third moveable sheave 22 and the fourth moveable sheave 24 five times prior to passing to the second storage reel 49.

The second storage reel 49 can be configured to receive the cable 12, and to apply a second tension 51 to the cable 12, thereby allowing tension in the cable 12 to be multiplied up to the test tension.

The tensioning of the cable 12 can occur at a speed from about one tenth of a foot per minute to about one thousand feet per minute. The tensioning of the cable 12 can occur at a load from about one hundred pounds of force to about sixty thousand pounds of force.

Figure 6:
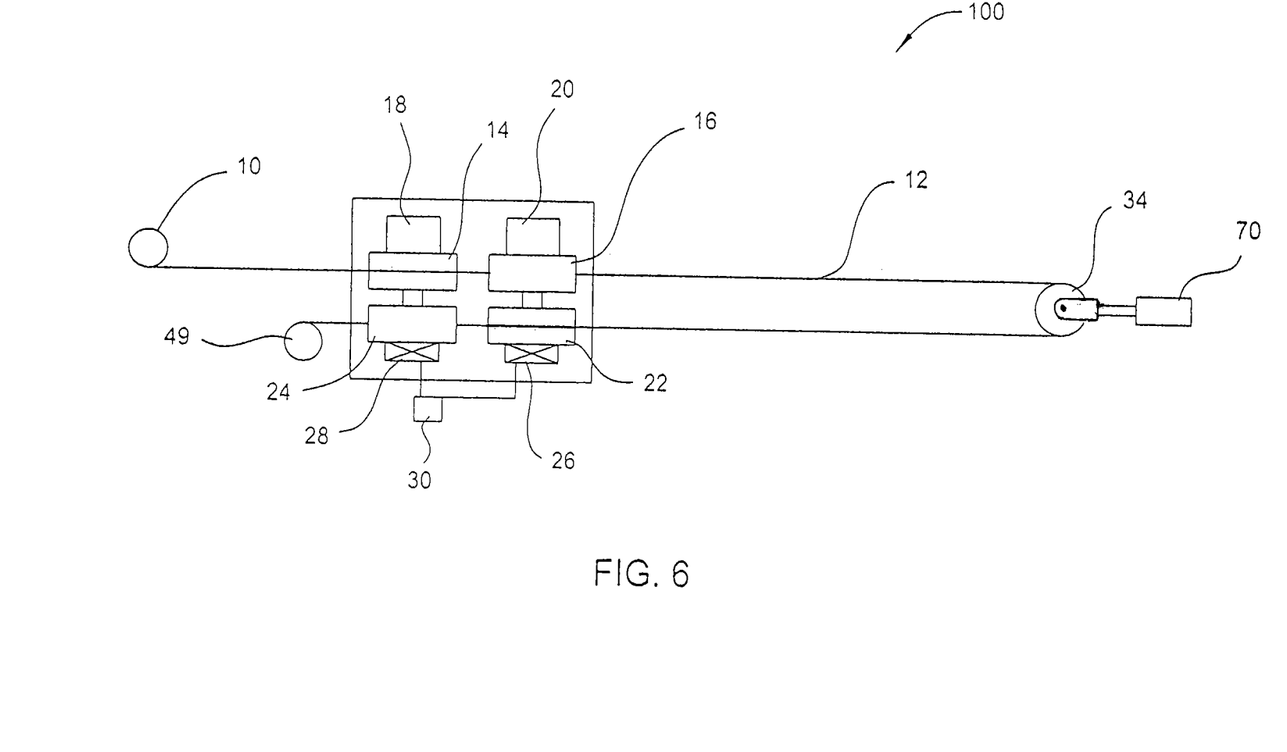
FIG. 6 is a simplified schematic representation of a portion of the hydraulic cycle test system shown in FIG. 1.

A simplified schematic representation of the hydraulic cycle test system 100 shown in FIG. 1 is shown in FIG. 6. The cable 12 is released from the first storage reel 10. The cable 12 then winds between the first moveable sheave 14 and second moveable sheave 16 before coupling to the moveable tensioning sheave 34. The cable 12 then winds between the third moveable sheave 22 and fourth moveable sheave 24 prior to storage in the second storage reel 49. The moveable tensioning sheave 34 is shown coupled to the hydraulic power source 70.

Figure 2:
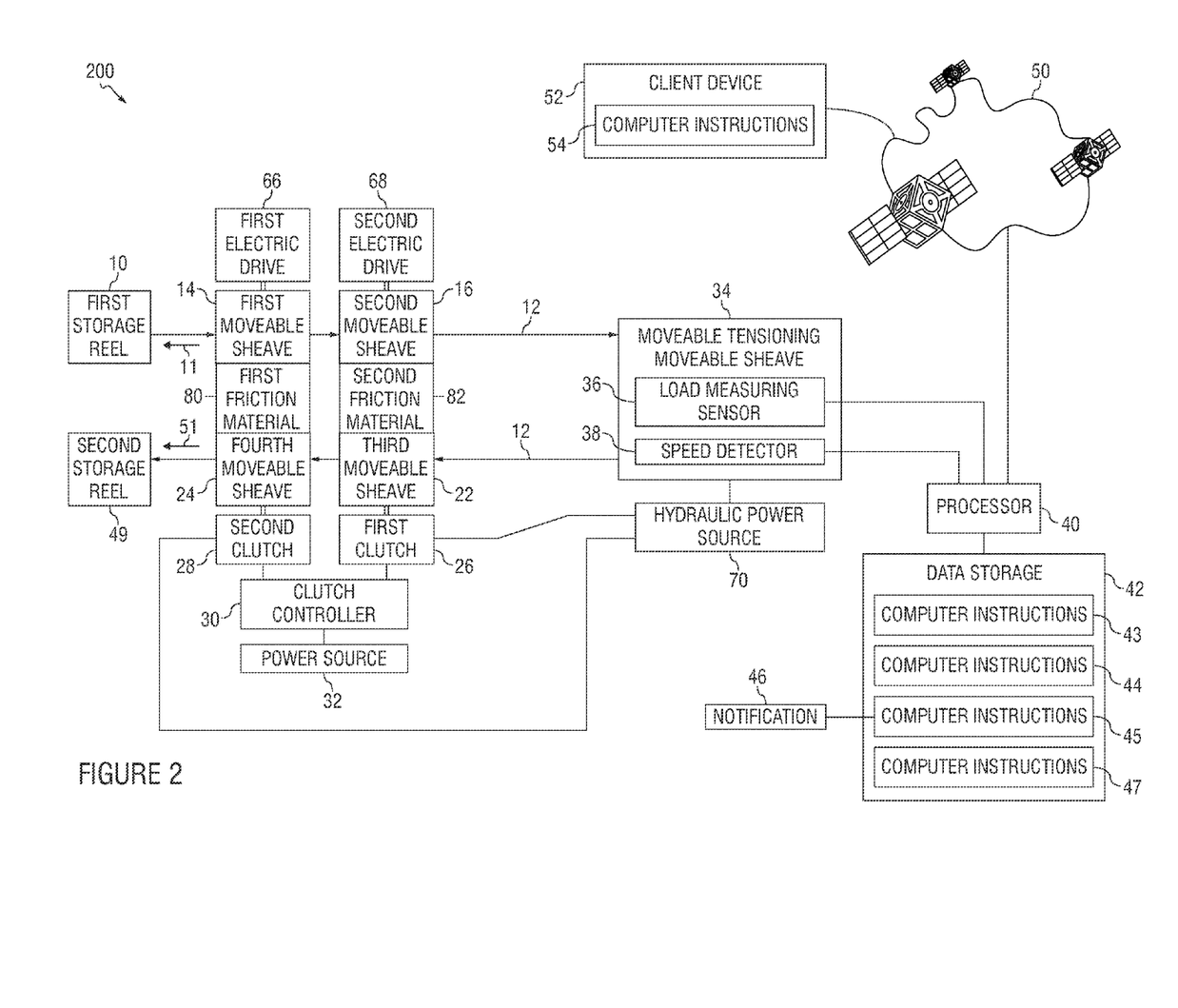
FIG. 2 depicts a schematic representation of an illustrative electrically operated cycle test system.

FIG. 2 depicts a schematic representation of an illustrative electrically operated cycle test system, according to one or more embodiments. The electrically operated system 200 can include a first electric drive 66 and a second electric drive 68 for driving the moveable sheaves 14, 16, 22, and 24. In addition, the hydraulic power source 70 can be in fluid communication with the first clutch 26 and the second clutch 28.

The operation of the electrically operated system 200 can be substantially similar to the operation of the hydraulically operated system 100 in FIG. 1. The first electric drive 66 can drive the first moveable sheave 14 and the fourth moveable sheave 24. The second electric drive 68 can drive the second moveable sheave 16 and the third moveable sheave 22. The hydraulic power source 70 can operate the first clutch 26 and the second clutch 28.

Figure 3:
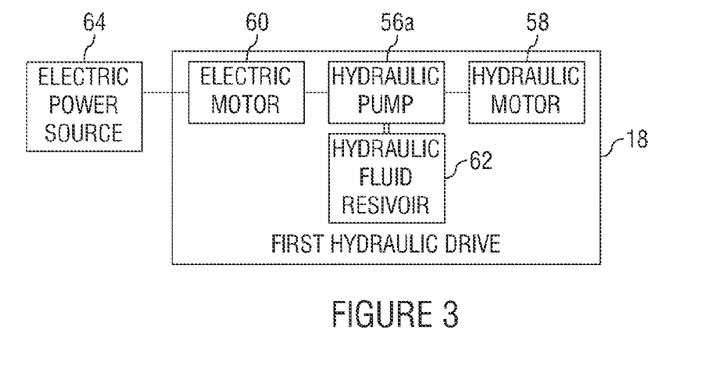
FIG. 3 depicts a schematic of an illustrative hydraulic drive.

FIG. 3 depicts a schematic of the first hydraulic drive 18, according to one or more embodiments. The first hydraulic drive 18 can include a hydraulic fluid reservoir 62, a hydraulic motor 58, a hydraulic pump 56a, and an electric motor 60. The electric motor 60 can be in communication with an electric power source 64. The second hydraulic drive can be substantially similar to the first hydraulic drive 18.

The hydraulic fluid reservoir 62 can be any fluid containment source, and can contain any hydraulic fluid. The hydraulic fluid reservoir 62 can be in fluid communication with the hydraulic pump 56a. The hydraulic pump 56a can be a centrifugal pump or another fluid pump. The hydraulic pump 56a can be in fluid communication with the hydraulic motor 58. The hydraulic pump 56a can be driven by the electric motor 60. The electric motor 60 can be a squirrel cage electric motor or another type of electric motor. The electric motor 60 can receive power from the electric power source 64, which can be an alternating current or direct current power source depending on the type of electric motor 60 used.

As the electric motor 60 drives the hydraulic pump 56a, the hydraulic pump 56a can provide a pump head to the fluid in the hydraulic fluid reservoir 62 and can flow the fluid from the hydraulic fluid reservoir 62 to the hydraulic motor 58. As such, the hydraulic pump 56a can drive the hydraulic motor 58 by moving the fluid in the hydraulic fluid reservoir 62 to the hydraulic motor 58. The hydraulic motor 58 can be directly and/or indirectly coupled to one or more of the moveable sheaves and can drive the coupled moveable sheaves.

Figure 4:
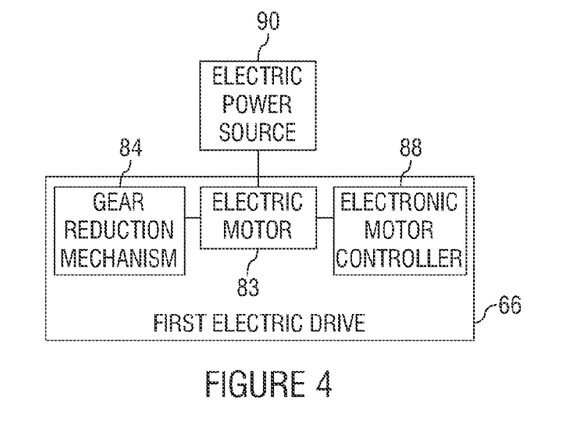
FIG. 4 depicts a schematic of an illustrative electric drive.

FIG. 4 depicts a schematic of an illustrative first electric drive 66, according to one or more embodiments. The first electric drive 66 can include an electric motor 83, a gear reduction mechanism 84, and an electronic motor controller 88. The electric motor 83 can be in communication with an electric power source 90.

The electric motor 83 can be an alternating current electric motor or a direct current motor. The electric motor 83 can be powered by the electric power source 90, and controlled by the electronic motor controller 88. The electronic motor controller 88 can be a variable speed controller, a digital speed controller, an on/of switch, or a combination thereof. The gear reduction mechanism 84 can directly and/or indirectly couple the electric motor 83 to one or more of the moveable sheaves and can drive one or more of the coupled moveable sheaves. The gear reduction mechanism 84 can be a speed reducer or a similar device, and can convert a portion of the speed of the electric motor to torque. The second electric drive can be substantially similar to the first electric drive.

Figure 5:
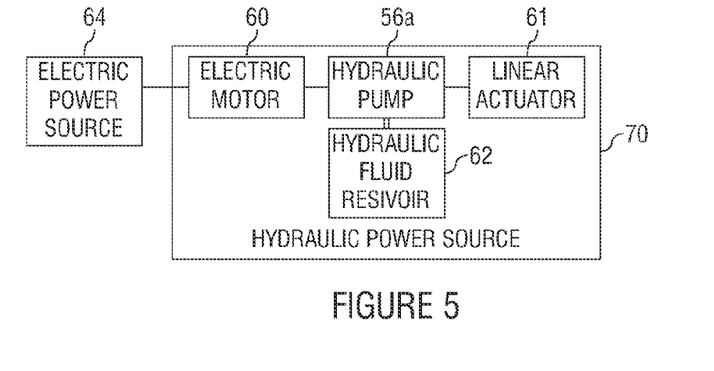
FIG. 5 depicts a schematic of an illustrative hydraulic power source.

FIG. 5 a schematic of an illustrative hydraulic power source 70, according to one or more embodiments. The hydraulic power source 70 can include one or more hydraulic pumps 56a, a linear actuator 61, one or more electric motors 60, and one or more hydraulic fluid reservoirs 62. The electric motor 60 can engage an electric power source 64.

The hydraulic power source 70 can include a plurality of hydraulic pumps. For example, the hydraulic power source 70 can have from about one hydraulic pump to about eight hydraulic pumps. The hydraulic pump 56a can be in fluid communication with the hydraulic fluid reservoir 62 and with the linear actuator 61. The electric motor 60 can be configured to drive the hydraulic pump 56a. Accordingly, the electric motor 60 can provide power to the hydraulic pump 56a to flow fluid from the hydraulic reservoir 62 to the linear actuator 61.

The electric power source 64 can be a four hundred sixty volt three-phase power supply or another power supply depending on the type of electric motor 60 used. The linear actuator 61 can be coupled to the moveable tensioning moveable sheave through a mechanical linkage.

While these embodiments have been described with emphasis on the embodiments, it should be understood that within the scope of the appended claims, the embodiments might be practiced other than as specifically described herein.

What is claimed is:

1. A hydraulic operated system for testing cable under tension, the system comprising:
   a. a first storage reel for paying out a cable to be tested;
   b. a first moveable sheave in series with a second moveable sheave, wherein the first moveable sheave is rotated by a first hydraulic drive, wherein the second moveable sheave is rotated by a second hydraulic drive, and wherein the first moveable sheave receives the cable from the first storage reel and passes the cable to the second moveable sheave;
   c. a third moveable sheave in series with a fourth moveable sheave, wherein the third moveable sheave is rotated by a second hydraulic drive, wherein the third moveable sheave is in parallel with the second moveable sheave, wherein the fourth moveable sheave is rotated by the first hydraulic drive, and wherein the fourth moveable sheave is in parallel with the first moveable sheave;
   d. a first clutch for connecting the second moveable sheave to the third moveable sheave, wherein the first clutch is operable by the second hydraulic drive, and wherein the first clutch disengages the second moveable sheave from the third moveable sheave;
   e. a second clutch connecting the first moveable sheave to the fourth moveable sheave, wherein the second clutch is operable by the first hydraulic drive, and wherein the second clutch disengages the first moveable sheave from the fourth moveable sheave;
   f. a clutch controller for controlling the first clutch and the second clutch, wherein the clutch controller is in communication with a power source;
   g. a moveable tensioning sheave connected to at least one of the hydraulic drives, wherein the moveable tensioning sheave comprises a load measuring sensor and a speed detector, wherein the moveable tensioning sheave receives the cable from the second moveable sheave, wherein the load measuring sensor measures a load on the cable forming a load signal, wherein the speed detector measures a speed of the cable forming a speed signal, wherein the moveable tensioning sheave passes the cable to the third moveable sheave which sequentially passes the cable to the fourth moveable sheave;

h. a processor in communication with the moveable tensioning sheave for receiving the load signal and the speed signal;

i. a data storage in communication with the processor;

j. computer instructions in the data storage for storing preset stress data for the cable;

k. computer instructions in the data storage for comparing received load signals and received speed signals to the stored preset stress data, and forming compared signals;

l. computer instructions in the data storage for providing a notification when the compared signals exceed or fall below the stored preset stress data;

m. computer instructions in the data storage for displaying the compared signals, the notification, or combinations thereof; and n. a second storage reel for receiving the cable from the fourth moveable sheave, wherein each moveable sheave comprises grooves for receiving the cable, wherein each groove contains the cable in parallel to transfer the cable from one moveable sheave to another moveable sheave, and wherein each groove is tilted in part, thereby enabling at least two opposing grooves to be aligned at bottoms of the moveable sheaves, but to be offset at tops of the moveable sheaves to facilitate transfer of the cable without sliding the cable on a face of each moveable sheave.

2. A hydraulic operated system for testing cable under tension, the system comprising:

a. a first storage reel for paving out a cable to be tested;

b. a first moveable sheave in series with a second moveable sheave, wherein the first moveable sheave is rotated by a first hydraulic drive, wherein the second moveable sheave is rotated by a second hydraulic drive, and wherein the first moveable sheave receives the cable from the first storage reel and passes the cable to the second moveable sheave;

c. a third moveable sheave in series with a fourth moveable sheave, wherein the third moveable sheave is rotated by a second hydraulic drive, wherein the third moveable sheave is in parallel with the second moveable sheave, wherein the fourth moveable sheave is rotated by the first hydraulic drive, and wherein the fourth moveable sheave is in parallel with the first moveable sheave;

d. a first clutch for connecting the second moveable sheave to the third moveable sheave, wherein the first clutch is operable by the second hydraulic drive, and wherein the first clutch disengages the second moveable sheave from the third moveable sheave;

e. a second clutch connecting the first moveable sheave to the fourth moveable sheave, wherein the second clutch is operable by the first hydraulic drive, and wherein the second clutch disengages the first moveable sheave from the fourth moveable sheave;

f. a clutch controller for controlling the first clutch and the second clutch, wherein the clutch controller is in communication with a power source;

g. a moveable tensioning sheave connected to at least one of the hydraulic drives, wherein the moveable tensioning sheave comprises a load measuring sensor and a speed detector, wherein the moveable tensioning sheave receives the cable from the second moveable sheave, wherein the load measuring sensor measures a load on the cable forming a load signal, wherein the speed detector measures a speed of the cable forming a speed signal, wherein the moveable tensioning sheave passes the cable to the third moveable sheave which sequentially passes the cable to the fourth moveable sheave;

h. a processor in communication with the moveable tensioning sheave for receiving the load signal and the speed signal;

i. a data storage in communication with the processor;

j. computer instructions in the data storage for storing preset stress data for the cable;

k. computer instructions in the data storage for comparing received load signals and received speed signals to the stored preset stress data, and forming compared signals;

l. computer instructions in the data storage for providing a notification when the compared signals exceed or fall below the stored preset stress data;

m. computer instructions in the data storage for displaying the compared signals, the notification, or combinations thereof; and (n.)—a second storage reel for receiving the cable from the fourth moveable sheave, wherein the first movable sheave is configured to pass the cable to the second moveable sheave, wherein the system is configured to wrap the cable about the first moveable sheave and the second moveable sheave five times prior to passing the cable from the second moveable sheave to the moveable tensioning sheave, wherein the moveable tensioning sheave is configured to pass the cable to the third moveable sheave, wherein the third moveable sheave is configured to pass the cable to the fourth moveable sheave, and wherein the system is configured to wrap the cable about the third moveable sheave and the fourth moveable sheave five times prior to passing the cable from the fourth moveable sheave to the second storage reel.

3. A hydraulic operated system for testing cable under tension, the system comprising:

a. a first storage reel for paving out a cable to be tested;

b. a first moveable sheave in series with a second moveable sheave, wherein the first moveable sheave is rotated by a first hydraulic drive, wherein the second moveable sheave is rotated by a second hydraulic drive, and wherein the first moveable sheave receives the cable from the first storage reel and passes the cable to the second moveable sheave;

c. a third moveable sheave in series with a fourth moveable sheave, wherein the third moveable sheave is rotated by a second hydraulic drive, wherein the third moveable sheave is in parallel with the second moveable sheave, wherein the fourth moveable sheave is rotated by the first hydraulic drive, and wherein the fourth moveable sheave is in parallel with the first moveable sheave;

d. a first clutch for connecting the second moveable sheave to the third moveable sheave, wherein the first clutch is operable by the second hydraulic drive, and wherein the first clutch disengages the second moveable sheave from the third moveable sheave;

e. a second clutch connecting the first moveable sheave to the fourth moveable sheave, wherein the second clutch is operable by the first hydraulic drive, and wherein the second clutch disengages the first moveable sheave from the fourth moveable sheave;

f. a clutch controller for controlling the first clutch and the second clutch, wherein the clutch controller is in communication with a power source;
g. a moveable tensioning sheave connected to at least one of the hydraulic drives, wherein the moveable tensioning sheave comprises a load measuring sensor and a speed detector, wherein the moveable tensioning sheave receives the cable from the second moveable sheave, wherein the load measuring sensor measures a load on the cable forming a load signal, wherein the speed detector measures a speed of the cable forming a speed signal, wherein the moveable tensioning sheave passes the cable to the third moveable sheave which sequentially passes the cable to the fourth moveable sheave;
h. a processor in communication with the moveable tensioning sheave for receiving the load signal and the speed signal;
i. a data storage in communication with the processor;
j. computer instructions in the data storage for storing preset stress data for the cable;
k. computer instructions in the data storage for comparing received load signals and received speed signals to the stored preset stress data, and forming compared signals;
l. computer instructions in the data storage for providing a notification when the compared signals exceed or fall below the stored preset stress data;
m. computer instructions in the data storage for displaying the compared signals, the notification, or combinations thereof; and
n. a second storage reel for receiving the cable from the fourth moveable sheave, wherein the further comprises:
a first friction material disposed between the first moveable sheave and the fourth moveable sheave for coupling the first moveable sheave and the fourth moveable sheave with the second clutch; and
a second friction material disposed between the second moveable sheave and the third moveable sheave for coupling the second moveable sheave and the third moveable sheave with the first clutch.

4. The system of claim 3, wherein the first friction material and the second friction material comprise a wearable brake material that locks pairs of moveable sheaves together during testing of the cable.

5. An electric operated system for testing cable under tension, the system comprising:
a. a first storage reel for paying out a cable to be tested;
b. a first moveable sheave in series with a second moveable sheave, wherein the first moveable sheave is rotated by a first electric drive, wherein the second moveable sheave is rotated by a second electric drive, and wherein the first moveable sheave receives the cable from the first storage reel and passes the cable to the second moveable sheave;
c. a third moveable sheave in series with a fourth moveable sheave, wherein the third moveable sheave is rotated by the second electric drive, wherein the third moveable sheave is in parallel with the second moveable sheave, wherein the fourth moveable sheave is rotated by the first electric drive, and wherein the fourth moveable sheave is in parallel with the first moveable sheave;
d. a first clutch connecting the second moveable sheave to the third moveable sheave, wherein the first clutch is operable by a hydraulic power source, and wherein the first clutch disengages the second moveable sheave from the third moveable sheave;
e. a second clutch connecting the first moveable sheave to the fourth moveable sheave, wherein the second clutch is operable by the hydraulic power source, and wherein the second clutch disengages the first moveable sheave from the fourth moveable sheave;
f. a clutch controller for controlling the first clutch and the second clutch, wherein the clutch controller is in communication with a power source;
g. a moveable tensioning sheave connected to the hydraulic power source, wherein the moveable tensioning sheave comprises a load measuring sensor for measuring a load of the cable to form a load signal and a speed detector to measure a speed of the cable to form a speed signal, wherein the moveable tensioning sheave receives the cable from the second moveable sheave and passes the cable to the third moveable sheave which sequentially passes the cable to the fourth moveable sheave;
h. a processor in communication with the moveable tensioning sheave for receiving the load signal and the speed signal;
i. a data storage in communication with the processor;
j. computer instructions in the data storage for storing preset stress data for the cable;
k. computer instructions in the data storage for comparing received load signals and received speed signals from the moveable tensioning sheave to the stored preset stress data, and forming compared signals;
l. computer instructions in the data storage for providing a notification when the compared signals exceed or fall below the stored preset stress data;
m. computer instructions in the data storage for displaying the compared signals, notifications, or combinations thereof; and
n. a second storage reel for receiving the cable from the fourth moveable sheave, wherein each of the moveable sheaves comprises grooves for receiving the cable, wherein the grooves contain the cable in parallel to transfer the cable from one moveable sheave to another moveable sheave, and wherein each groove is tilted in part enabling at least two opposing grooves to be aligned at bottoms of the moveable sheaves, but to be offset at tops of the moveable sheaves to facilitate cable transfer without sliding the cable on a face of the moveable sheaves.

6. An electric operated system for testing cable under tension, the system comprising:
a. a first storage reel for paying out a cable to be tested;
b. a first moveable sheave in series with a second moveable sheave, wherein the first moveable sheave is rotated by a first electric drive, wherein the second moveable sheave is rotated by a second electric drive, and wherein the first moveable sheave receives the cable from the first storage reel and passes the cable to the second moveable sheave;
c. a third moveable sheave in series with a fourth moveable sheave, wherein the third moveable sheave is rotated by the second electric drive, wherein the third moveable sheave is in parallel with the second moveable sheave, wherein the fourth moveable sheave is rotated by the first electric drive, and wherein the fourth moveable sheave is in parallel with the first moveable sheave;
d. a first clutch connecting the second moveable sheave to the third moveable sheave, wherein the first clutch is operable by a hydraulic power source, and wherein the first clutch disengages the second moveable sheave from the third moveable sheave;
e. a second clutch connecting the first moveable sheave to the fourth moveable sheave, wherein the second clutch is operable by the hydraulic power source, and wherein the second clutch disengages the first moveable sheave from the fourth moveable sheave;

f. a clutch controller for controlling the first clutch and the second clutch, wherein the clutch controller is in communication with a power source;
g. a moveable tensioning sheave connected to the hydraulic power source, wherein the moveable tensioning sheave comprises a load measuring sensor for measuring a load of the cable to form a load signal and a speed detector to measure a speed of the cable to form a speed signal, wherein the moveable tensioning sheave receives the cable from the second moveable sheave and passes the cable to the third moveable sheave which sequentially passes the cable to the fourth moveable sheave;
h. a processor in communication with the moveable tensioning sheave for receiving the load signal and the speed signal;
i. a data storage in communication with the processor;
j. computer instructions in the data storage for storing preset stress data for the cable;
k. computer instructions in the data storage for comparing received load signals and received speed signals from the moveable tensioning sheave to the stored preset stress data, and forming compared signals;
l. computer instructions in the data storage for providing a notification when the compared signals exceed or fall below the stored preset stress data;
m. computer instructions in the data storage for displaying the compared signals, notifications, or combinations thereof; and
n. a second storage reel for receiving the cable from the fourth moveable sheave, wherein the first moveable sheave is configured to pass the cable to the second moveable sheave, wherein the system is configured to wrap the cable about the first moveable sheave and the second moveable sheave five times prior to passing the cable from the second moveable sheave to the moveable tensioning sheave, wherein the moveable tensioning sheave is configured to pass the cable to the third moveable sheave, wherein the third moveable sheave is configured to pass the cable to the fourth moveable sheave, and wherein the system is configured to wrap the cable five times about the third moveable sheave and the fourth moveable sheave prior to passing the cable from the fourth moveable sheave to the second storage reel.

7. An electric operated system for testing cable under tension, the system comprising:
a. a first storage reel for paying out a cable to be tested;
b. a first moveable sheave in series with a second moveable sheave, wherein the first moveable sheave is rotated by a first electric drive, wherein the second moveable sheave is rotated by a second electric drive, and wherein the first moveable sheave receives the cable from the first storage reel and passes the cable to the second moveable sheave;
c. a third moveable sheave in series with a fourth moveable sheave, wherein the third moveable sheave is rotated by the second electric drive, wherein the third moveable sheave is in parallel with the second moveable sheave, wherein the fourth moveable sheave is rotated by the first electric drive, and wherein the fourth moveable sheave is in parallel with the first moveable sheave;
d. a first clutch connecting the second moveable sheave to the third moveable sheave, wherein the first clutch is operable by a hydraulic power source, and wherein the first clutch disengages the second moveable sheave from the third moveable sheave;
e. a second clutch connecting the first moveable sheave to the fourth moveable sheave, wherein the second clutch is operable by the hydraulic power source, and wherein the second clutch disengages the first moveable sheave from the fourth moveable sheave;
f. a clutch controller for controlling the first clutch and the second clutch, wherein the clutch controller is in communication with a power source;
g. a moveable tensioning sheave connected to the hydraulic power source, wherein the moveable tensioning sheave comprises a load measuring sensor for measuring a load of the cable to form a load signal and a speed detector to measure a speed of the cable to form a speed signal, wherein the moveable tensioning sheave receives the cable from the second moveable sheave and passes the cable to the third moveable sheave which sequentially passes the cable to the fourth moveable sheave;
h. a processor in communication with the moveable tensioning sheave for receiving the load signal and the speed signal;
i. a data storage in communication with the processor;
j. computer instructions in the data storage for storing preset stress data for the cable;
k. computer instructions in the data storage for comparing received load signals and received speed signals from the moveable tensioning sheave to the stored preset stress data, and forming compared signals;
l. computer instructions in the data storage for providing a notification when the compared signals exceed or fall below the stored preset stress data;
m. computer instructions in the data storage for displaying the compared signals, notifications, or combinations thereof; and
n. a second storage reel for receiving the cable from the fourth moveable sheave, wherein the further comprises
  a first friction material disposed between the first moveable sheave and the fourth moveable sheave for coupling the first moveable sheave and the fourth moveable sheave with the second clutch; and
  a second friction material disposed between the second moveable sheave and the third moveable sheave for coupling the second moveable sheave and the third moveable sheave with the first clutch.

8. The system of claim 7, wherein the first friction material and the second friction material comprise a wearable brake material that locks the moveable sheaves together during testing of the cable to be tested.

9. A system for testing cable under tension, the system comprising:
a. a first storage reel configured to payout a cable to be tested;
b. a first moveable sheave configured to receive the cable from the first storage reel;
c. a first drive coupled with the first moveable sheave, wherein the first drive is configured to rotate the first moveable sheave;
d. a second moveable sheave in series with the first moveable sheave and configured to receive the cable from the first moveable sheave;
e. a second drive coupled with the second moveable sheave, wherein the second drive is configured to rotate the second moveable sheave;
f. a moveable tensioning sheave coupled to at least one of the drives, wherein the moveable tensioning sheave comprises:
  (i) a load measuring sensor for measuring a load of the cable forming a load signal; and
  (ii) a speed detector for measuring a speed of the cable, forming a speed signal, wherein the moveable tensioning sheave is in series with the second moveable sheave, and wherein the moveable tensioning sheave is configured to receive the cable from the second moveable sheave;

g. a third moveable sheave in series with the moveable tensioning sheave and configured to receive the cable from the moveable tensioning sheave, wherein the second drive is coupled with the third moveable sheave for rotating the third moveable sheave;

h. a fourth moveable sheave in series with the third moveable sheave, wherein the first drive is coupled with the fourth moveable sheave for rotating the fourth moveable sheave, and wherein the fourth moveable sheave is configured to receive the cable from the third moveable sheave;

i. a second storage reel configured to receive the cable from the fourth moveable sheave;

j. a first clutch coupling the second moveable sheave to the third moveable sheave, wherein the first clutch is operable by one of the drives, a hydraulic power source, or combinations thereof, and wherein the first clutch is configured to disengage the second moveable sheave from the third moveable sheave;

k. a second clutch coupling the first moveable sheave to the fourth moveable sheave, wherein the second clutch is operable by one of the drives, the hydraulic power source, or combinations thereof, and wherein the second clutch is configured to disengage the first moveable sheave from the fourth moveable sheave;

l. a clutch controller for controlling the first clutch and the second clutch;

m. a processor in communication with the moveable tensioning sheave for receiving the load signal and the speed signal therefrom;

n. a data storage in communication with the processor comprising preset stress data for the cable stored therein;

o. computer instructions in the data storage to instruct the processor to compare the received load signal and the received speed signal to the stored preset stress data, and form compared signals;

p. computer instructions in the data storage to instruct the processor to provide a notification when the received load signal, the received speed signal, or combinations thereof exceed or fall below the stored preset stress data; and q. computer instructions in the data storage to instruct the processor to display the compared signals, the notification, or combinations thereof, wherein the system further comprises:

a first friction material disposed between the first moveable sheave and the fourth moveable sheave for coupling the first moveable sheave and the fourth moveable sheave with the second clutch; and a second friction material disposed between the second moveable sheave and the third moveable sheave for coupling the second moveable sheave and the third moveable sheave with the first clutch.

* * * * *

UNITED STATES PATENT AND TRADEMARK OFFICE
CERTIFICATE OF CORRECTION

PATENT NO.         : 8,577,627 B1
APPLICATION NO.    : 12/886762
DATED              : November 5, 2013
INVENTOR(S)        : Joe R. Janac et al.

Page 1 of 1

It is certified that error appears in the above-identified patent and that said Letters Patent is hereby corrected as shown below:

In the Claims:

Column 9, Claim 2, Line 37, please delete "paving" and insert -- paying -- therefor;

Column 10, Claim 2, Line 26, please delete "movable" and insert -- moveable -- therefor;

Column 10, Claim 3, Line 43, please delete "paving" and insert -- paying -- therefor;

Column 11, Claim 3, Line 31, please insert -- system -- after the;

Column 14, Claim 7, Line 32, please insert -- system -- after the.

Signed and Sealed this
Eleventh Day of March, 2014

Michelle K. Lee
*Deputy Director of the United States Patent and Trademark Office*